United States Patent
Bliss et al.

[11] Patent Number: 5,896,854
[45] Date of Patent: Apr. 27, 1999

[54] TRACHEAL GAS INSUFFLATION SYSTEM

[75] Inventors: Peter L. Bliss, Prior Lake; Robert W. McCoy, Apple Valley; Alexander B. Adams, Minneapolis, all of Minn.

[73] Assignee: Valley Inspired Products, LLC, Minneapolis, Minn.

[21] Appl. No.: 09/072,525

[22] Filed: May 4, 1998

[51] Int. Cl.$^6$ .................................................. A61M 15/00
[52] U.S. Cl. .......................... 128/200.24; 128/204.18; 128/204.23; 128/207.14
[58] Field of Search ................. 128/200.26, 207.14, 128/204.18, 204.23, 200.24

[56] References Cited

U.S. PATENT DOCUMENTS

| | | | |
|---|---|---|---|
| 5,186,167 | 2/1993 | Kolobow | 128/207.14 |
| 5,255,675 | 10/1993 | Kolobow | 128/207.14 |
| 5,291,882 | 3/1994 | Makhoul et al. | 128/207.14 |
| 5,400,778 | 3/1995 | Jonson et al. | 128/207.14 |
| 5,419,314 | 5/1995 | Christopher | 128/200.26 |
| 5,544,648 | 8/1996 | Fischer, Jr. | 128/207.14 |
| 5,606,968 | 3/1997 | Mang | 128/207.14 |
| 5,687,714 | 11/1997 | Kolobow et al. | 128/207.14 |
| 5,697,364 | 12/1997 | Chua et al. | 128/207.14 |

OTHER PUBLICATIONS

"Tracheal Gas Insufflation: Adjunct to Conventional Mechanical Ventilation", *Respiratory Care*, Feb., 1996, vol. 41, No. 2, pp. 105–111.

The Effect of Tracheal Gas Insufflation (TGI), Negative Expiratory Airway Pressure (NEAP) and TGI–NEAP Combined on Autopeep in a Lung Model, Takahashi T., et al, University of Minnesota–St. Paul Ramsey Medical Center, Abstract, presented at American Assoc. of Respiratory Care in New Orleans, Dec. 1997.

"Negative Expiratory Airway Pressure (NEAP) and Tracheal Gas Insufflation (TGI) in Combination Augments CO2 Elimination More Than TGI Alone", Takahashi T., et al, University of Minnesota–St. Paul Ramsey Medical Center, Abstract, presented at American Thoracic Mtg. in Chicago, Apr. 1998.

Product literature, Taema, Air Liquide Healthcare.

*Primary Examiner*—Aaron J. Lewis
*Attorney, Agent, or Firm*—Nikolai, Mersereau & Dietz, P.A.

[57] ABSTRACT

A system for flushing carbon dioxide from ventilation equipment so that the carbon dioxide is not rebreathed by the patient. Flushing is achieved by providing tracheal gas insufflation only during the end of the patient's expiratory phase.

8 Claims, 2 Drawing Sheets

TRACHEAL GAS INSUFFLATION SYSTEM

The present invention relates to ventilators used in medical treatment. More specifically, the present invention relates to a system for flushing carbon dioxide, in a controlled and safe fashion, from ventilator equipment.

BACKGROUND OF THE INVENTION

I. Field of the Invention

The prior art includes numerous ventilators and ancillary equipment used in patient care. This equipment serves the vital purpose of supplying life sustaining oxygen to the patient's lungs. Many significant developments have been made in ventilator equipment since it was first introduced. Yet even the most sophisticated equipment available in the prior art suffers from one very significant problem, the accumulation of $CO_2$ over time can greatly impair the health of a patient who would not be receiving treatment via a ventilator, but for the patient's already poor health.

II. Description of the Prior Art

The adverse effects of accumulation of carbon dioxide in the "dead spaces" of a ventilator or patient's airway have been known since the 1960's. Since that time, doctors have attempted to bypass the dead spaces of the mouth and upper airway by employing a tracheostomy. When a tracheostomy is employed, the air to be inhaled never passes through the mouth or upper airway where carbon dioxide can accumulate. More recently, a technique known as tracheal gas insufflation has been used to "flush" carbon dioxide from the dead spaces of the ventilator and the patient's airway.

Tracheal gas insufflation is the introduction of a low flow of oxygen or air into the endotracheal tube of a mechanically ventilated patient. The gas is directed through a small catheter or secondary pathway to the distal end of the endotracheal tube. This serves to introduce the oxygen or air just above the carina and flush the carbon dioxide from the endotracheal tube so the patient does not "rebreathe" the carbon dioxide with the next breath.

Traditionally, tracheal gas insufflation has been applied in a continuous flow manner. This has several disadvantages. First, the continuous flow dries out secretions making them difficult to remove. Second, continuous flow can dry mucosa resulting in tissue damage. Third, the additional gas flow adds to the desired tidal volume and end expiratory pressure making the ventilator settings inaccurate. Fourth, the additional gas flow increases the effort required for the patient to trigger the ventilator.

SUMMARY OF THE INVENTION

In view of the negative effects of accumulated carbon dioxide and tracheal gas insufflation as it has been previously administered, there is a real need for a system that successfully flushes carbon dioxide so that it is not rebreathed and yet minimizes the negative effects of tracheal gas insufflation. All of this is achieved by the present invention which monitors the patient's flow rate and triggers intermittent application of tracheal gas insufflation in accordance with a predetermined algorithm and clinician set parameters. Rather than applying tracheal gas insufflation continuously, the present invention applies tracheal gas insufflation only late in the expiratory phase when it can properly flush out the exhaled carbon dioxide without the adverse side effects noted above.

The present invention will become better understood from a reading of the following Detailed Description of the Invention and the appended claims in view of the drawings in which corresponding parts are identified with corresponding numbers in the several views.

DETAILED DESCRIPTION OF THE PREFERRED EMBODIMENTS

Figure 1:
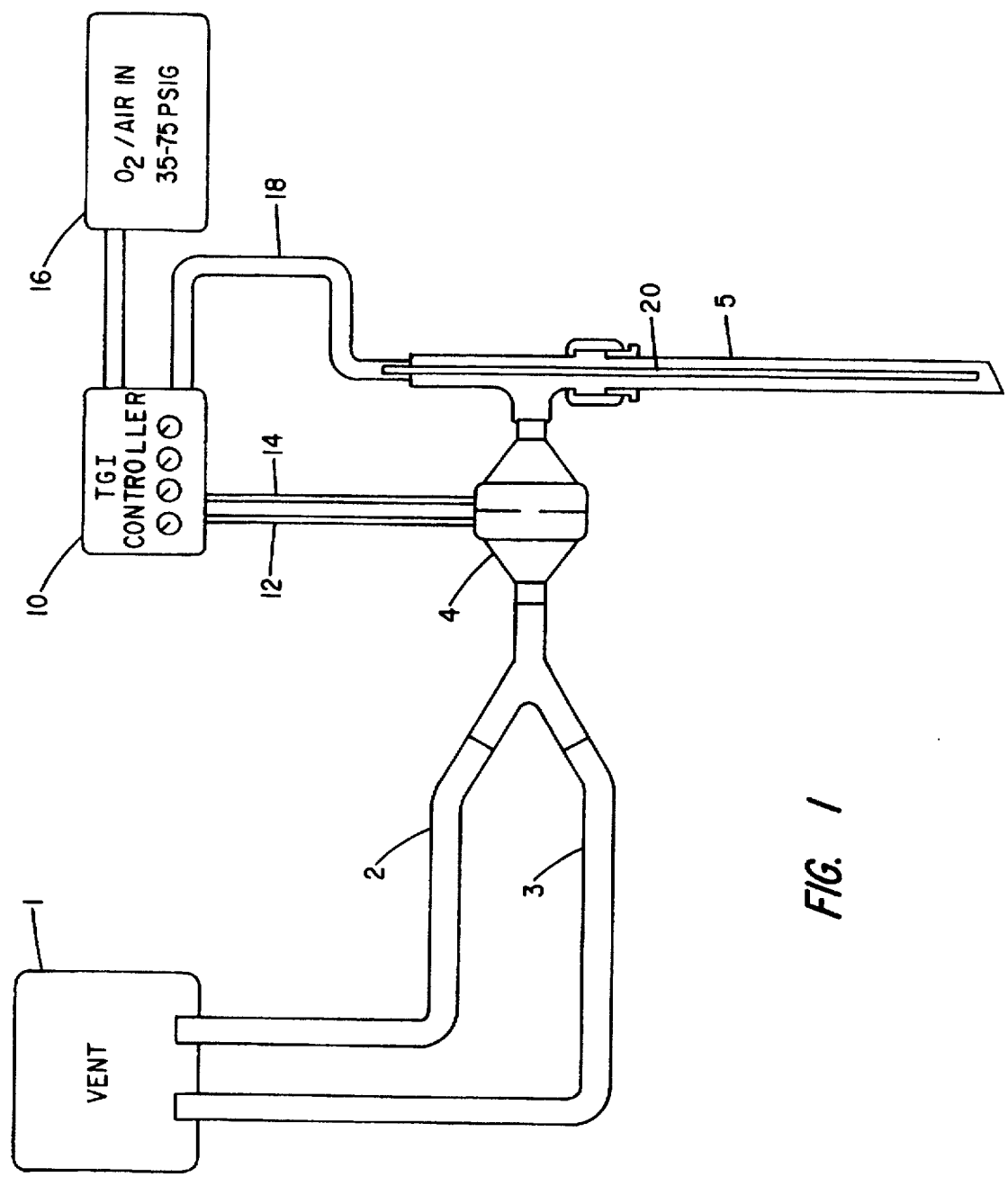
FIG. 1 is a schematic diagram showing the present invention.

FIG. 1, in schematic form, shows a ventilator 1 coupled by tubes 2 and 3 to a flow meter 4, i.e. pneumotachometer. The flow meter 4 is, in turn, coupled to an endotracheal tube 5 which is designed to be inserted into a patient's throat for delivery of ventilation therapy. FIG. 1 also shows a tracheal gas insufflation (TGI) controller 10. The TGI controller 10 is coupled to the flow meter 4 by a pair of leads 12 and 14 so that it can sense changes in flow indicative of ventilation events. The TGI controller 10 also is coupled to a gas source 16 and a gas delivery tube 18 which is coupled to a TGI catheter 20. The TGI catheter 20 resides within the endotracheal tube 5. Given this configuration, the TGI controller 10 can monitor the ventilation therapy and cooperate with the gas source 16, the gas delivery tube 18 and the TGI catheter 20 to deliver gas which flushes the endotracheal tube 5 and other surrounding dead spaces where exhaled carbon dioxide might otherwise accumulate.

Figure 2:
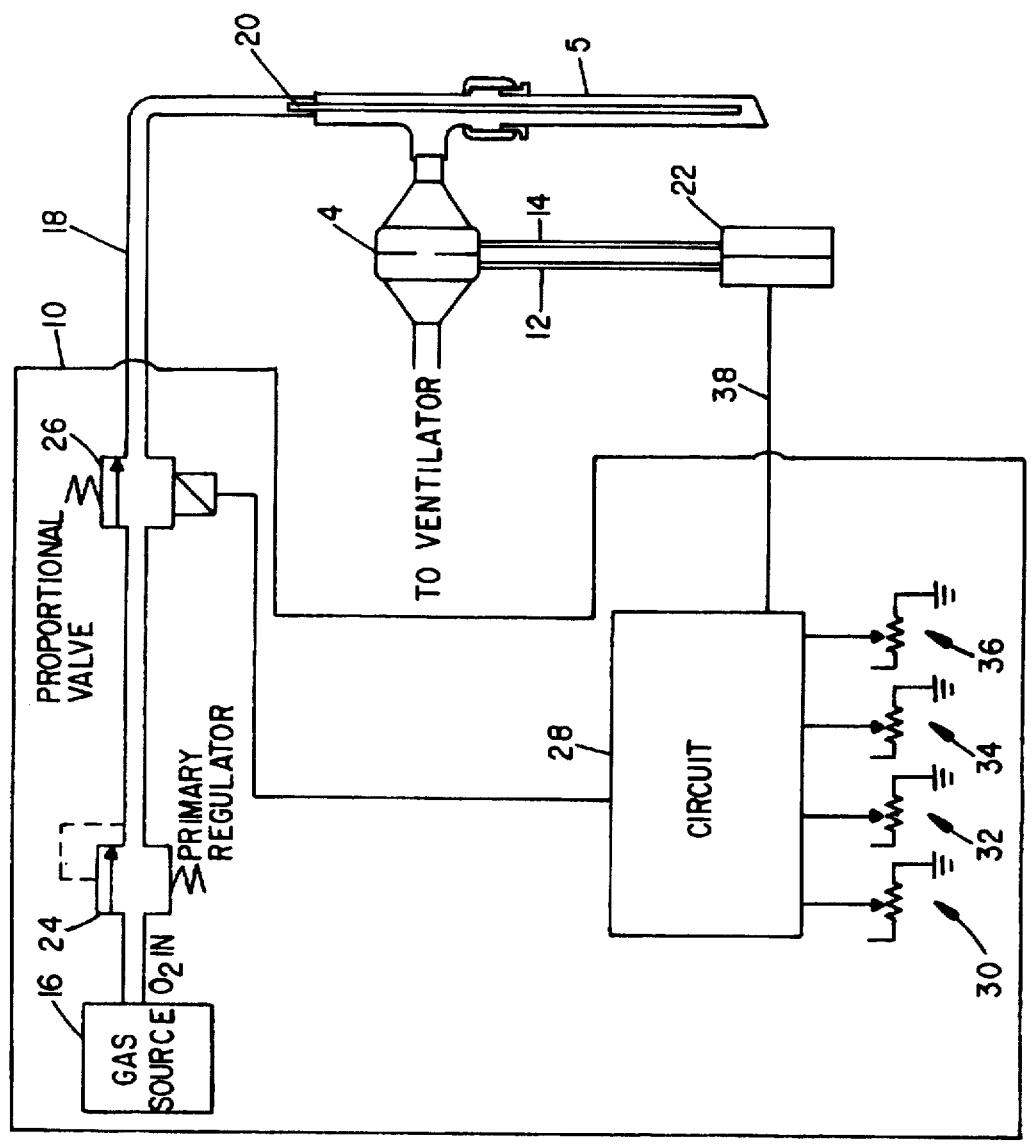
FIG. 2 is a schematic diagram of the tracheal gas insufflation controller and the manner in which it cooperates with the other structures incorporated within the present invention.

FIG. 2 shows in greater detail the structure of the TGI controller 10 and the structure which allows it to cooperate with the rest of the apparatus to flush exhaled gases. As shown in FIG. 2, the TGI controller includes a flow meter 22, a primary regulator 24, a proportional valve 26, and a control circuit 28 coupled to four potentiometers 30, 32, 34 and 36 and to the pressure transducer by an electrical connection 38.

The control circuit 28 is, in essence, a programmable digital computer and will typically include a processor, random accesses memory, read only memory, one or more analog-to-digital converters, and other components typically associated with a computer used for control purposes. The computer of the control circuit has a program stored in memory and responds to various inputs based upon this program to generate control signals to the actuator (typically a solenoid) of the proportional valve 26. Inputs received by the control circuit 28 include signals received from potentiometers 30, 32, 34 and 36. TGI "flow rate" is governed by potentiometer 30. The ventilation flow rate at which valve 26 is opened is governed by potentiometer 32. Potentiometer 34 is used to set the ventilation flow rate at which the valve 26 closes. Potentiometer 36 can be used to set a maximum time that valve 26 is allowed to remain open.

Now that the components of the present invention have been described, the advantages of the invention can be better understood. The principal advantage of the present invention is that the negative effects associated with applying tracheal gas insufflation in a continuous flow manner can be minimized. This is achieved by limiting the time that the flow is applied. The most effective time for delivering such flow is at the very end of exhalation. During the inspiratory phase of respiration, tracheal gas insufflation flow does nothing that the ventilator is not already doing. Early in the expiratory phase, tracheal gas insufflation gases are washed out of the endotracheal tube by the patient's exhaled gases. Only the tracheal insufflation gases delivered during the end of the expiratory phase serve to properly flush out the CO₂ containing exhaled gas and replace the exhaled gas with air or oxygen as desired.

The controller of the present invention monitors the patient's flow rate and triggers the tracheal gas insufflation flow on and off based upon a predetermined program and parameters set by the clinician using the potentiometers. Based upon the program, changes in flow sensed by the flow meter 22 and the potentiometer settings established by the clinician, the control circuit controls actuation of the proportional valve 26. The proportional valve is maintained in its closed position during the inspiratory phase and during the bulk of the expiratory phase. Only after expiratory flow is decreasing does the controller 10 actuate the proportional valve 26 to open the valve 26 allowing tracheal gas insufflation gases to flow through the tube 18 to the TGI catheter 20. During this phase the TGI gas serves to flush the endotracheal tube and surrounding area. When the flow meter 22 detects a sharp drop in expiratory flow, indicating an inspiratory effort is about to begin, the controller 10 again sends a control signal to the solenoid of the proportional valve 26 causing the proportional valve 26 to close. Thus, no TGI is delivered during the inspiratory phase and the valve is not opened again until after expiratory flow begins to decrease. Given the configuration of the controller 10, the clinician can set the flow rate, the flow rate at which TGI is initiated, the flow rate at which TGI is ceased, and the maximum time during which TGI is delivered during any breath cycle. Again, this is accomplished using potentiometers 30, 32, 34 and 36. Alternatively, the program could be modified so that after initiation of TGI, the valve 26 would remain open for a predetermined period of time settable using one of the potentiometers.

It should now be clear, the present invention permits CO₂ to be flushed from the endotracheal tube and other surrounding dead spaces so that carbon dioxide is not rebreathed by the patient. Also, because TGI is not delivered continuously but rather only at the point in time where it does the most good, the controller 10 allows for more precise control of the ventilator and also prevents some of the adverse effects of continuous TGI identified above. Finally, because the controller 10 responds to changes in flow rather than pressure, greater accuracy can be achieved. If pressure (rather than flow) were sensed, the controller would not turn off the TGI flow until the ventilator provided a positive pressure. This would make it more difficult for the patient to trigger the ventilator to provide a breath.

What is claimed:

1. For use by an operator in conjunction with a ventilator and a tube such as an endotracheal tube or tracheostomy tube, used to ventilate a patient, an apparatus for flushing carbon dioxide from said tube, said apparatus comprising:
   (1) a gas source,
   (2) means for delivering gas from the gas source to the end of a tube;
   (3) a valve coupled to said gas source and to said delivery tube so that when said valve is open gas flows from the gas source through said delivery tube and catheter to flush a tube;
   (4) a flow meter for generating signals indicative of the flow of gas within tube;
   (5) a programmable controller coupled to said valve and said flow meter, said controller being operable to open and close said valve in accordance with a programmed set of instructions and in response to said signals generated by said low meter and at least one parameter set by an operator said programmable controller operating to open the valve during the end portion of a patient's expiratory phase and closing the valve no later than the commencement of such a patient's inspiratory phase.

2. The apparatus of claim 1 wherein said at least one parameter set by an operator includes the rate at which gas will flow when the valve is open.

3. The apparatus of claim 1 wherein said at least one parameter set by an operator incudes the flow rate sensed by the flow meter that will cause the controller to open said valve.

4. The apparatus of claim 1 wherein said at least one parameter set by an operator includes the flow rate sensed by the flow meter that will cause the controller to close said valve.

5. The apparatus of claim 1 wherein said at least one parameter set by the operator includes the maximum time the controller will allow the valve to remain open.

6. The apparatus of claim 1 wherein said at least one parameter set by an operator includes: (a) the flow rate sensed by the flow meter which will cause the valve to open; (b) the flow rate sensed by the flow meter which will cause the valve to close; and (c) the maximum time the valve will be open in any one cycle of the valve.

7. The apparatus of claim 6 wherein said at least one parameter also includes the rate at which gas will flow past the valve, when the valve is open.

8. The apparatus of claim 1 wherein said means for delivering gas from the gas source to said tube is a delivery tube coupled to a catheter.

* * * * *

UNITED STATES PATENT AND TRADEMARK OFFICE
CERTIFICATE OF CORRECTION

PATENT NO. : 5,896,854
DATED : April 27, 1999
INVENTOR(S) : Peter L. Bliss, et al It is certified that error appears in the above-indentified patent and that said Letters Patent is hereby corrected as shown below:

```
Claim 1, column 4, line 14 before "tube" insert -- a --;
line 19 delete "low" and insert -- flow --.
```

Signed and Sealed this

Seventh Day of September, 1999

Attest:

Q. TODD DICKINSON

Attesting Officer

Acting Commissioner of Patents and Trademarks